| United States Patent [19] | [11] Patent Number: 4,914,195 |
| Ogura et al. | [45] Date of Patent: Apr. 3, 1990 |

[54] PROCESS FOR PREPARING N-ACETYLNEURAMINIC ACID DERIVATIVES

[75] Inventors: Haruo Ogura, Matsudo; Kimio Furuhata, Tokyo; Yoshiyasu Shitori, Musashino; Masayoshi Ito, Kunitachi, all of Japan

[73] Assignee: MECT Corporation, Japan

[21] Appl. No.: 664,686

[22] Filed: Nov. 26, 1984

Related U.S. Application Data

[63] Continuation of Ser. No. 387,528, Jun. 11, 1982, abandoned.

[30] Foreign Application Priority Data

Jun. 26, 1981 [JP] Japan .................................. 56-99364

[51] Int. Cl.[4] ............................................. C08B 37/00
[52] U.S. Cl. ..................................... 536/53; 536/55.3; 536/18.7
[58] Field of Search ........................ 536/53, 55.3, 18.7

[56] References Cited

PUBLICATIONS

Kuhn et al., Chem. Ber., 99, 611 (1966).

*Primary Examiner*—Alan Siegel
*Attorney, Agent, or Firm*—Jacobs & Jacobs

[57] ABSTRACT

A new process for preparing halides of N-acetylneuraminic acids useful as an intermediate in preparing new N-acetylneuraminic acid derivatives having an excellent immunological activity is provided, which process comprises simultaneously acetylating and halogenating an esterified N-acetylneuraminic acid with the aid of an acetyl halide, and according to the process, the halides may be obtained in high yield of about 90%.

6 Claims, No Drawings

PROCESS FOR PREPARING N-ACETYLNEURAMINIC ACID DERIVATIVES

CROSS-REFERENCE

This is a continuation of Ser. No. 387,528 filed June 11, 1982 now abandoned.

BACKGROUND OF THE INVENTION

The present invention relates to a process for preparing halides of N-acetylneuraminic acid which are particularly useful as a starting material for the preparation of new N-acetylneuraminic acid derivatives having an excellent immunological activity.

The halides of N-acetylneuraminic acid represented by the following general formula [I]:

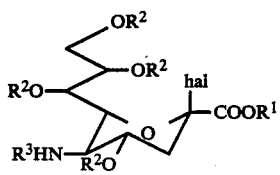

wherein $R^1$ is a lower alkyl or a non-substituted or lower alkyl substituted aralkyl or aryl group, $R^2$ and $R^3$ represent hydrogen atom or acetyl group independently and hal represents a halogen atom, particularly chlorides thereof are known as explained below. The compounds [I] are useful as a starting material for preparing immunologically active derivatives of N-acetylneuraminic acid which are clinically expected as an immunosuppressive, in particular to treat autoimmune disease such as collagenosis disease without causing any serious side-effects (see, for example Japanese Patent Application No. 77672/1981).

Therefore, it is medically and pharmaceutically important to develop a new, simple and economical process which provides the compounds [I] in high yield.

Conventionally, a known process for preparing the compounds [I] is the process of Richard Kuhn et al. disclosed in Chem. Ber., 99, 611 (1966) which comprises the steps of esterifying N-acetylneuraminic acid as a starting material to prepare methyl β-D-N-acetylneuraminate (step 1), acetylating the acetylneuraminate derivative to obtain methyl 4,7,8,9-tetra-O-acetyl-β-D-N-acetylneuraminate (step 2) and chlorinating said acetylated derivative to form methyl 2-chloro-4,7,8,9-tetra-O-acetyl-β-D-N-acetylneuraminate (step 3).

According to the process of R. Kuhn et al., at the first step the esterified derivative may be obtained as a yield of 97% crude product and about 60% purified product and at the second step the objective acetylated derivative may be prepared by treating the esterified derivative with acetic anhydride under the presence of perchloric acid catalyst and extracting the product with chloroform, in an yield of 61%. However, in the reexamination carried out by the inventors of the present invention, the yield of said second step is found to be at most 60%. While at the third step the crude acetylated derivative is treated with acetylchloride solution saturated with hydrogen chloride gas at −40° to −60° C. under moderate pressure condition and the final product is obtained in a yield of 80%. However, in this third step, there are problems in economy and safety of the reaction condition.

Therefore, in the process of R. Kuhn et al. there still remains room for improvement.

SUMMARY OF THE INVENTION

Under such circumstances, the present inventors exhaustively studied and investigated the process of R. Kuhn et al. to improve it in yield, economy and safety of operations and found that the above-mentioned disadvantages of said process may effectively be eliminated by carrying out the acetylation and the chlorination steps simultaneously.

The principal object of the invention is to provide a process for preparing N-acetylneuraminic acid derivatives, in particular halides thereof which are useful as a starting material or an intermediate for the preparation of immunologically active N-acetylneuraminic acid derivatives.

Another purpose of the invention is to improve the process of R. Kuhn et al. in yield, safety of operations and economy.

A further object of this invention is to provide a new process for preparing immunologically active N-acetylneuraminic acid derivatives.

The said and other objects as well as features of the present invention will be more apparent from the explanation hereinafter described.

According to the present invention, halides of N-acetylneuraminic acid represented by the general formula [I] may be prepared by esterifying N-acetylneuraminic acid with an alcohol such as methanol, ethanol, benzylalcohol according to a conventional method and then simultaneously acetylating and halogenating the resultant esterified N-acetylneuraminic acid with acetylhalide.

In the simultaneous acetylation and halogenation process of the present invention, the reaction temperature is not critical, however, usually room temperature (about 20° to 25° C.) is used from the economical point of view and these reactions sufficiently proceed by simply agitating the reaction solution for several hours. It is possible to recover the objective product in high yield (95%) by distilling off the excess amount of acetylhalide after the simultaneous reaction, without any extraction procedures.

The halides of the present invention may also be prepared by simultaneously acetylating and halogenating a compound of the formula [I']:

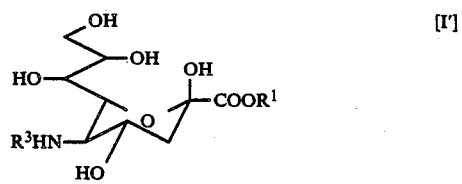

wherein $R^1$ has the same meaning as defined above and $R^3$ is hydrogen atom or acetyl group.

One of the starting material in which $R^3$ is hydrogen may easily be prepared from N-acetylneuraminic acid by deacetylation.

The processes of the present invention and of R. Kuhn et al. are hereinbelow illustrated for the purpose of comparison:

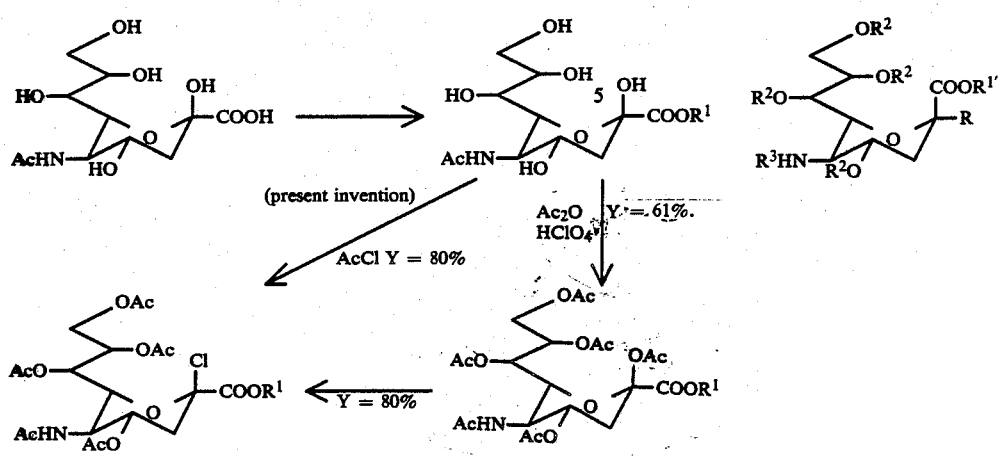

(wherein Y represents yield)

Comparing the two cases in overall yield of the pure product, the yield of R. Kuhn et al. is 29.3% (0.60×0.61×0.80×100), while that of the present invention is 76% (0.95×0.8×100). Thus, according to the process of the present invention, the objective product can be obtained in an yield about 22% three times higher than that attained by the process of R. Kuhn et al. Furthermore, in the re-examination carried out by the inventors of the present invention, the overall yield of R. Kuhn et al. becomes at most 32.4% (0.6×0.6×0.9×100). Therefore, in such case, the yield of this invention is approximately two times greater than that of R. Kuhn et al.

In addition, the product according to the process of this invention is more excellent than the product obtained by the process of R. Kuhn et al. in particular in purity (by-products produced being small), optical purity and degree of halogenation. This is because the product of the present invention provides colorless needle crystal having a melting point of 116°–118° C. by the recrystallization from a mixed solvent of benzene-ether-petroleum ether, while the literature of R. Kuhn et al. does not disclose melting point thereof and from the results of the re-examination carried out by the present inventors the product obtained according to the process of R. Kuhn et al. can not be crystallized.

Consequently, it will be appreciated that the process of the present invention is considerably effective in view of the yield, safety and economy, to prepare N-acetylneuraminic acid derivatives which are useful as a starting material for the preparation of immunologically active N-acetylneuraminic acid derivatives and therefore, the process of this invention may be significantly effective in industry.

R. Kuhn et al., in said paper, simply disclose the molecular formula of a halide of N-acetylneuraminic acid derivative (chloride) and do not disclose the melting point thereof as mentioned above. Such being the case, we believe that we are the pioneer in confirming the said chloride.

The product may react with a nucleoside or a gluocose and if desired the resulting product may be deacetylated to form immunologically active N-acetylneuraminic acid derivatives [II] according to Koenigs-Knorr reaction:

wherein $R^{1'}$ represents hydrogen atom, lower alkyl or a non-substituted or lower alkyl substituted aralkyl or aryl group, R stands for a residue of a nucleoside or a glucose and $R^2$ and $R^3$ have the same meaning as defined above.

Said Koenigs-Knorr reaction may be carried out under the presence of a catalyst such as $Ag_2CO_2$, $Ag_2O$, $AgClO_4$, $Hg(CN)_2$, $HgBr_2$ and in a preferred embodiment, it is desirable to use a molecular sieve such as molecular sieve 3 A or 4 A together with said catalyst so that hydrogen halides generated during the reaction may effectively be removed and a high yield may be attained.

The reaction temperature is not critical, however, the reaction is usually carried out at room temperature from the economical point of view and the simplicity of the operation.

The reaction period may be in a range of from 30 minutes to 24 hours.

Acetonitrile or nitromethane may preferably be used as a reaction medium in the present invention.

The deactylation reaction may be carried out according to a process which comprises agitating the product having acetyl group(s), obtained after the Koenigs-Knorr reaction, at a temperature of −20° to 0° C. for about 20 minutes in a reaction medium such as methanol, under the presence of an alkali metal alcoholate, neutralizing the reaction solution with Dowex 50×8 (H+) and thereafter treating the product according to a conventional procedures.

Now, the present invention will be explained more in concretely referring to the following non-limitative examples.

EXAMPLE 1

Preparation of methyl 2-chloro-4,7,8,9-tertra-O-acetyl-$\beta$-D-N-acetylneuraminate.

N-Acetylneuraminic acid (1 g) was dissolved in methanol (100 ml) and 2 g of Dowex 50×8 (H+) was added to said solution. The mixture was agitated at room temperature for 2 hours, then filtered and the filtrate was evaporated to dryness. The resultant residue was recrystallized from methanol-ether and 1 g of methyl $\beta$-D-N-acetyl-neuraminate was obtained as a colorless needle crystal (yield 95%).

Physical properties:

m.p. 175°–178° C. $[\alpha]_D^{20} -28°$ (c=1, $H_2O$)

Elemental analysis: $C_{12}H_{21}NO_9$: calculated: C 44.58;

H 6.55; H 4.33; found: C 44.62; H 6.57; H 4.23.

To 1 g of methyl β-D-N-acetyl-neuraminate thus obtained, 10 ml of acetyl chloride was added and the mixture was stirred at room temperature for 5 hours, the excess amount of acetylchloride was distilled off under reduced pressure, then benzene was added to the solution and the solvent was again distilled off to obtain 1.5 g (yield 95%) of the title compound as colorless amorphous substance. The crude substance was recrystallized from benzene-ether-petroleum ether mixed solvent and obtained 1.26 g (yield 80%) of the title compound as colorless needle crystal.

Physical properties:
m.p. 116°–118° C.
$[α]_D^{20} -68°$ (c=1, chloroform)
I.R. $ν_{max}^{KBr}$ (cm$^{-1}$) 1735, 1654, 1532
$^1$H NMR (CDCl$_3$) $δ_H$ (TMS) 1.92 (3H, s), 1.99–2.10 (OAc×4), 2.87 (1H, dd, J=5.0 and 12.0 Hz), 3.91 (3H, s)

EXAMPLE 2

Preparation of 2′,3′-di-O-acetyl-5′-o-(4-N-acetyl-2,4-dideoxy-3,6,7,8-tetra-O-acetyl-1-methoxycarbonyl-D-glycero-α-D-galacto-octopyranosyl) inosine.

To 30 ml of acetonitrile, 550 mg of 2′,3′-di-O-acetylinosine, 150 mg of Hg(CN)$_2$, 300 mg of HgBr$_2$ and 500 mg of molecular sieve (4 A) were added, further 510 mg of methyl 2-chloro-4,7,8,9-tetra-O-acetyl-β-D-N-acetylneuraminate (compound obtained in the example 1) was added to said mixture and the mixture was agitated at room temperature for 48 hours. The resultant solution was filtered and the filtrate was evaporated to dryness. To the residue, 50 ml of ethyl acetate was added and the solution was washed two times with 30% potassium iodide solution to remove Hg(CN)$_2$ and HgBr$_2$. The solution was dried over Glauber's salt and the solvent was distilled off. Purification was established by subjecting the crude product to alumina column chromatography and eluting with benzene-ethylacetate. The title compound was obtained in an amount of 430 mg (yield 52%) as colorless powder.

Physical properties:
$[α]_D^{25} -16°$ (c=1, methanol)
Elemental analysis: C$_{34}$H$_{43}$N$_5$O$_{19}$: calculated: C 49.46; H 5.25; N 8.48; found: C 49.15; H 5.41; N 8.11.
Mass Spectroscopy (FD) m/z 825 (M+)
I.R. $ν_{max}^{KBr}$ (cm$^{-1}$) 3300, 1740, 1660, 1530
$^1$H NMR (CDCl$_3$) $δ_H$ (TMS) 1.88–2.20 (OAc×7), 2.76 (1H, dd, J=13.0 and 4.5 Hz), 3.78 (3H, s), 5.95 (1H, d, J=2.2 Hz), 8.20 (1H, s), 8.44 (1H, s)

EXAMPLE 3

Preparation of 5-fluoro-2′,3′-isopropylidene-5′-O-(4-N-acetyl-2,4-dideoxy-3,6,7,8,-tetra-O-acetyl-1-methoxy-carbonyl-D-glycero-α-D-galacto-octopyranosyl)-uridine.

To a solution of 5-fluoro-2′,3′-isopropylideneuridine (500 mg), 150 mg of Hg(CN)$_2$ and 300 mg of HgBr in 30 ml of acetonitrile, 510 mg of the compound obtained in the Example 1 was added and the mixture was stirred at room temperature for 24 hours. The reaction solution was filtered, the filtrate was distilled off under reduced pressure at 40° C. and evaporated to dryness. To the resultant residue, 100 ml of ethylacetate was added and the solution was washed with 30% potassium iodide aqueous solution, to remove Hg(CN)$_2$ and HgBr$_2$. The ethylacetate solution was dried over Glauber's salt and then the solvent was distilled off. From the residue obtained, ether-soluble substances were removed and then 10 ml of chloroform was added to remove insoluble materials. To the chloroform spolution, ether was added to form precipitates, and the crystals were filtered off and dried. Thus, 62 mg of colorless powder was obtained.

Physical properties:
$[α]_D^{25} -1.4°$ (c=1, methanol)
Elemental analysis: C$_{32}$H$_{42}$N$_3$O$_{18}$F: calculated: C 49.55; H 5.42; N 5.45; found: C 49.24; H 5.80; N 5.12.
Mass Spectroscopy: m/z 775 (M+), 760 (M+-15), 732 (M+-43), 716 (M+-59)
I.R. $ν_{max}^{KBr}$ (cm$^{-1}$): 1735, 1680, 1530
$^1$H NMR (CDCl$_3$) $δ_H$(TMS): 1.48 (3H, s), 1.74 (3H, s), 1.89 (3H, s), 2.08 (6H, s), 2.20 (6H, s), 3.80 (B 3H, s), 5.95 (1H, d, J=2.0 Hz), 7.62 (1H, d, J=7 Hz)

What is claimed is:

1. A process for preparing acid derivatives represented by the following general formula (I):

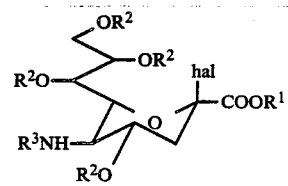

wherein R$^1$ is methyl R$^2$ and R$^3$ represent acetyl group and hal represents a halogen atom, characterized by simultaneously acetylating and halogenating an acid of the formula:

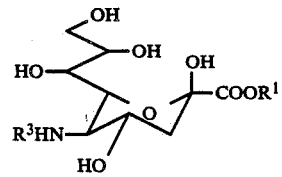

wherein R$^1$ and R$^3$ represent the same meaning as defined above,
at a temperature of from about 20° to 25° C. in the presence of acetylchloride.

2. A process for preparing acid derivatives having the following general formula (I):

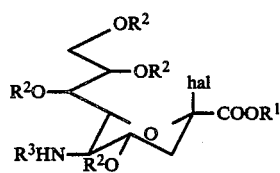

wherein R$^1$ is a lower alkyl or a non-substituted or lower alkyl substituted aralkyl or aryl group, R$^2$ and R$^3$ represent hydrogen atom or acetyl group independently and hal means a halogen atom,
comprising the steps of esterifying N-acetylneuraminic acid and simultaneously acetylating and halogenating the resultant esterified acid of the formula [I″]:

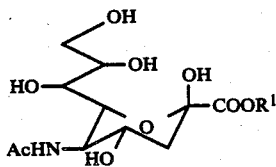

[I″]

wherein $R^1$ has the same meanings as defined above, at a temperature of from about 20° to 25° C. and in the presence of an acetylhalide.

3. A process as set forth in claim 2 wherein said esterification step is carried out by using methanol.

4. A process for preparing immunologically active acid derivatives represented by the general formula:

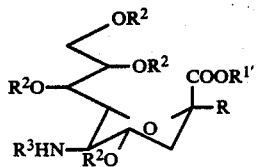

wherein R stands for a residue of a nucleoside or a glucose, $R^{1'}$ represents hydrogen atom, a lower alkyl or a non-substituted or lower alkyl substituted aralkyl or aryl group and $R^2$ and $R^3$ represent hydrogen atom or acetyl group independently, which comprises the steps of:

(i) esterifying N-acetylneuraminic acid,
(ii) simultaneously acetylating and halogenating the resulting esterified product at a temperature of from about 20° to 25° C. and in the presence of an acetylhalide to form a compound of the formula:

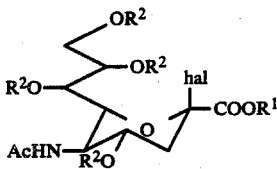

wherein $R^1$ is a lower alkyl or a non-substituted or lower alkyl substituted aralkyl or aryl grup, hal means a halogen atom and $R^2$ is the same meaning as defined above, (iii) subjecting the product obtained to Koenigs-Knorr reaction together with a nucleoside or a glucose, and
(iv) optionally deacetylating the resultant product.

5. A process as set forth in claim 4 wherein said esterification is carried out by using methyl alcohol.

6. A process as set forth in claim 5 wherein said nucleoside or glucose is a member selected from the group consisting of 5-fluoro-2′,3′-isopropylidene-uridine, 2′,3′-isopropylideneuridine, 2′,3′-di-O-acetylinosine, β-D-glucopyranose and 1,2,3,4-tetra-O-acetyl-β-D-glucopyranose.

* * * * *